United States Patent
Fan et al.

(10) Patent No.: US 11,543,232 B2
(45) Date of Patent: Jan. 3, 2023

(54) 3D INTRAORAL CAMERA USING FREQUENCY MODULATION

(71) Applicant: Carestream Dental Technology Topco Limited, London (GB)

(72) Inventors: Chuanmao Fan, Rochester, NY (US); Victor C. Wong, Pittsford, NY (US)

(73) Assignee: DENTAL IMAGING TECHNOLOGIES CORPORATION, Atlanta, GA (US)

(*) Notice: Subject to any disclaimer, the term of this patent is extended or adjusted under 35 U.S.C. 154(b) by 574 days.

(21) Appl. No.: 16/476,141

(22) PCT Filed: Jan. 5, 2017

(86) PCT No.: PCT/US2017/012274
§ 371 (c)(1),
(2) Date: Jul. 5, 2019

(87) PCT Pub. No.: WO2018/128611
PCT Pub. Date: Jul. 12, 2018

(65) Prior Publication Data
US 2019/0343377 A1    Nov. 14, 2019

(51) Int. Cl.
*G01B 9/02004*    (2022.01)
*A61B 1/24*    (2006.01)
(Continued)

(52) U.S. Cl.
CPC ............ *G01B 9/02004* (2013.01); *A61B 1/24* (2013.01); *A61B 5/0066* (2013.01); *A61B 5/0088* (2013.01); *G01B 9/02003* (2013.01); *G01B 11/2441* (2013.01); *G01S 17/34* (2020.01); *G01S 17/89* (2013.01)

(58) Field of Classification Search
CPC ............ G01B 9/02004; G01B 9/02003; G01B 11/2441; A61B 1/24; A61B 5/0066;
(Continued)

(56) References Cited

U.S. PATENT DOCUMENTS 7,733,497 B2 * 6/2010 Yun .................... G01B 9/02083
356/497
2009/0316966 A1 * 12/2009 Marshall .............. G06T 19/00
382/128
(Continued)

FOREIGN PATENT DOCUMENTS

EP    3213675 A1 *    9/2017    ......... A61B 1/00163

OTHER PUBLICATIONS

Arseny Vasilyev, Naresh Satyan, Shengbo Xu, George Rakuljic, and Amnon Yariv, "Multiple source frequency-modulated continuous-wave optical reflectometry: theory and experiment," Appl. Opt. 49, 1932-1937 (2010) (Year: 2010).*
(Continued)

Primary Examiner — John R Schnurr
(74) Attorney, Agent, or Firm — Alston & Bird LLP

(57) ABSTRACT

An apparatus for oral imaging has a light source energizable to generate a light frequency signal ranging from a minimum to a maximum frequency. An image acquisition apparatus scans the generated light frequency signal to successive positions on a sample surface and to combine a returned signal from each successive position with the generated light frequency signal. The image acquisition apparatus has a detector that obtains a beat frequency signal from the combined returned signal and the generated light frequency signal. A processor that is in signal communication with the detector generates a processed beat signal from the combined signals, wherein the processed beat signal is indicative of the distance from the tunable laser source to the sample surface at the corresponding position. A display is in signal communication with the processor and is energizable to display distance data according to the processed beat signal for each scanned position.

17 Claims, 12 Drawing Sheets

(51) Int. Cl.
*A61B 5/00* (2006.01)
*G01B 9/02003* (2022.01)
*G01B 11/24* (2006.01)
*G01S 17/89* (2020.01)
*G01S 17/34* (2020.01)

(58) Field of Classification Search
CPC ..... A61B 5/0088; A61B 5/0073; G01S 17/34; G01S 17/89
See application file for complete search history.

(56) References Cited

U.S. PATENT DOCUMENTS

| | | |
|---|---|---|
| 2012/0156638 A1 | 6/2012 | Gantes |
| 2012/0176626 A1 | 7/2012 | Qualding et al. |
| 2013/0182260 A1* | 7/2013 | Bonnema ............ A61B 5/0062 356/479 |
| 2018/0128900 A1* | 5/2018 | Al Hadi .................. G01S 7/481 |
| 2018/0310825 A1* | 11/2018 | Kakuma ............ A61B 1/00172 |
| 2019/0029505 A1* | 1/2019 | Kakuma ............... A61B 5/0066 |
| 2019/0117078 A1* | 4/2019 | Sharma ................... A61B 1/24 |

OTHER PUBLICATIONS

WIPO Application No. PCT/US2017/012274, PCT International Preliminary Report on Patentability dated Jul. 9, 2019.
WIPO Application No. PCT/US2017/012274, PCT International Search Report dated Apr. 18, 2017.
WIPO Application No. PCT/US2017/012274, PCT Written Opinion of the International Searching Authority dated Apr. 18, 2017.

* cited by examiner

Mach-Zehnder

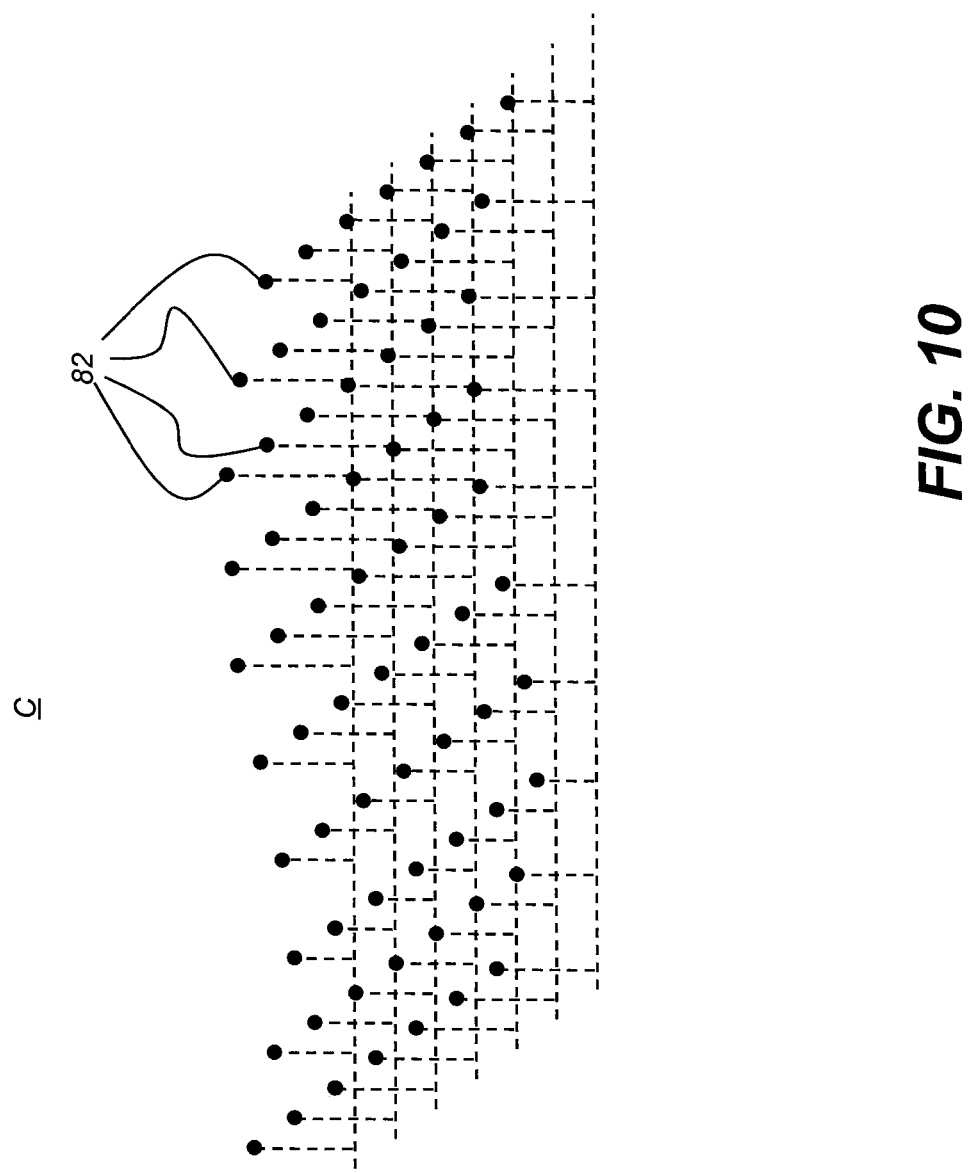

3D INTRAORAL CAMERA USING FREQUENCY MODULATION

FIELD OF THE INVENTION

The disclosure relates generally to 3-dimensional (3-D) surface imaging and more particularly relates to an intraoral imaging apparatus that uses frequency-modulated continuous-wave interference to characterize the surface structure of teeth and other intraoral features.

BACKGROUND OF THE INVENTION

Volume imaging of the teeth and related structures offers significant promise for various types of analysis, diagnosis, and treatment procedures. While accurate volume image data can be obtained using systems that generate and direct x-ray radiation through the patient, such as cone-beam computed tomography (CBCT) systems, there can be a number of assessment and treatment procedures that use light and do not require exposure of the patient to ionizing radiation. A number of types of imaging apparatus have been proposed for using advanced illumination, detection, and processing techniques that can reveal structural information from features inside the mouth without the complication and cost of x-ray systems hardware.

Optical coherence tomography (OCT) is one type of non-invasive imaging technique that employs interferometric principles to obtain high resolution, cross-sectional tomographic images that characterize the depth structure of a sample.

Particularly suitable for in vivo imaging of human tissue, OCT has shown its usefulness in a range of biomedical research and medical imaging applications, such as in ophthalmology, dermatology, oncology, and other fields, as well as in ear-nose-throat (ENT) and dental imaging. In an OCT imaging system, light from a wide-bandwidth source, such as a super luminescent diode (SLD) or other light source, is directed along two different optical paths: a reference arm of known length and a sample arm that illuminates the tissue or other subject under study. Reflected and back-scattered light from the reference and sample arms is then recombined in the OCT apparatus and interference effects are used to determine characteristics of the surface and near-surface underlying structure of the sample. Interference data can be acquired by rapidly scanning the sample illumination across the sample. At each of several thousand points, OCT apparatus obtains an interference profile which can be used to reconstruct an A-scan with an axial depth into the material. For most tissue imaging applications, OCT uses broadband illumination sources and can provide image content at depths of a few millimeters (mm).

While OCT offers considerable advantages for dental surface applications, there are some drawbacks to OCT imaging. OCT measurement is practical only over relatively small areas of a surface, requiring a substantial amount of calculation in order to provide useful data. OCT acquisition time is too slow for imaging more than a small area at a time, such as a few hundred $mm^2$. OCT measurements require probe placement relatively close to the surface of interest and, in practice, cannot be easily obtained over a large area. The field of view of the OCT device is necessarily constrained, precluding its practical use for obtaining surface data needed for generating digital impressions of a patient's face, for example.

Thus, it can be seen that there would be advantages to surface imaging methods that overcome the constraints of OCT and other measurement techniques in utility and that can be adapted for use in an intraoral imaging apparatus.

SUMMARY OF THE INVENTION

It is an object of the present disclosure to advance the art of 3D surface imaging using non-ionizing light energy. Another object of this application is to address, in whole or in part, at least the foregoing and other deficiencies in the related art. It is another object of this application to provide, in whole or in part, at least the advantages described herein. Certain exemplary method and/or apparatus embodiments herein can obtain surface contour images by employing Frequency-Modulated Continuous-Wave interferometry in a hand-held intraoral imaging camera.

These objects are given only by way of illustrative example, and such objects may be exemplary of one or more embodiments of the invention. Other desirable objectives and advantages inherently achieved by the disclosed methods may occur or become apparent to those skilled in the art. The invention is defined by the appended claims.

According to an aspect of the present disclosure, there is provided an apparatus for oral imaging can include a tunable laser source energizable to generate a light frequency signal that ranges from a first or minimum frequency to a different second or maximum frequency, an image acquisition apparatus that is energizable to scan the generated light frequency signal to each of a plurality of successive positions on a sample surface and to combine a returned signal from each successive sample surface position with the generated light frequency signal, the image acquisition apparatus having a detector that obtains a beat frequency signal corresponding to each scanned position from the combined returned signal and the generated light frequency signal; a processor that is in signal communication with the detector and that generates a processed beat signal from the obtained beat frequency, where the processed beat signal is indicative of a distance from the tunable laser source to the sample surface at the corresponding scanned position; and a display that is in signal communication with the processor and is energizable to display distance data according to the processed beat signal for each scanned position.

BRIEF DESCRIPTION OF THE DRAWINGS

The foregoing and other objects, features, and advantages of the invention will be apparent from the following more particular description of exemplary embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of described exemplary embodiments, such as support components used for providing power, for packaging, and for mounting and protecting system optics, for example, are not shown in the drawings in order to simplify description.

FIG. 10 shows a point cloud generated using the method and apparatus of the present disclosure.

DESCRIPTION OF EXEMPLARY EMBODIMENTS

Figure 1:
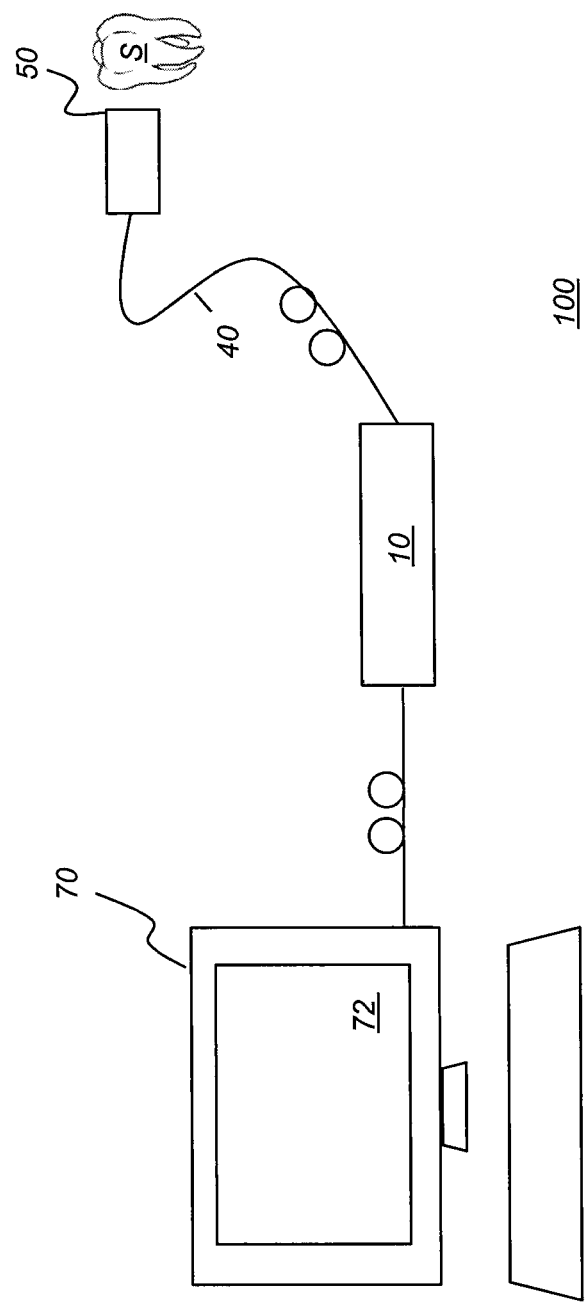
FIG. 1 is a schematic diagram that shows an intraoral 3-D imaging apparatus that uses Frequency-Modulated Continuous-Wave (FMCW) measurement.

The following is a description of exemplary method and/or apparatus embodiments of the application, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the term "optics" is used generally to refer to lenses and other refractive, diffractive, and reflective components or apertures used for shaping and orienting a light beam. An individual component of this type is termed an optic.

In the context of the present disclosure, the terms "viewer", "operator", and "user" are considered to be equivalent and can refer to the viewing practitioner, technician, or other person who may operate an intraoral camera or scanner and may also view and manipulate an image from such a device, such as a dental image, on a display monitor. An "operator instruction" or "viewer instruction" is obtained from explicit commands entered by the viewer, such as by clicking a button on the camera or scanner or by using a computer mouse or by touch screen or keyboard entry or other instruction entry mechanism.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the terms "camera" and "scanner" may be used interchangeably, as the description can relate to an image capture device that acquires image data in multiple modes, such as reflective color or monochrome images, contour images obtained from structured light, and image content acquired using interferometry imaging techniques.

Reference is made to Jesse Zheng, *Optical Frequency-Modulated Continuous-Wave (FMCW) Interferometry*, Springer Series in Optical Sciences, pp. 1-38, 99-119, and 224-233. Further reference is made to E. Baumann, F. R. Giorgetta, J.-D. Deschenes, W. C. Swann, I. Coddington, and N. R. Newbury, "Comb-calibrated laser ranging for three-dimensional surface profiling with micrometer-level precision at a distance," *Optics Express* 22, 24914-24928 (2014).

Frequency-Modulated Continuous Wave (FMCW) imaging for 3-D surface characterization has been used for obtaining information on position and speed of an object using an electromagnetic signal transmitted, then reflected from a target. With the advent of compact tunable lasers, FMCW has found a number of applications using optical energy, such as in Lidar (Light Detection and Ranging) or LADAR (laser detection and ranging), used for aerial imaging and laser guidance, for example. By comparison with OCT and related imaging methods, FMCW offers the potential for highly accurate surface characterization at high speeds. Unlike OCT and other interferometric methods that can obtain distance, depth, and range information for small areas of a surface, with sensor positioning very close to the surface of interest such as 10 mm or less, FMCW can be used to characterize variably sized surfaces and allows sensor positioning over a wide range of distances, even exceeding 1 m from the subject. This allows the same camera to operate as both an intraoral image capture apparatus for characterizing individual teeth and an extra-oral image capture apparatus for characterizing surfaces of the face and head, for example. The weight and dimensional footprint of an FMCW apparatus can improve upon what is available with OCT and other surface imaging approaches.

Although it provides highly accurate surface information that can be used for generating a point cloud of the sample surface, FMCW does not provide depth information for tissue beneath the sample surface, as does OCT. Because it presents more complex light handling and data manipulation than OCT and other methods, FMCW has not been widely adapted for use in hand-held imaging apparatus, such as those employed for intra-oral or other medical imaging.

FMCW surface measurement requires a continuous wave (CW) laser source that generates light in a range of frequencies, generated in a linear progression. The generated CW light is directed toward a target subject or sample surface. With each scan of frequencies, the laser light that is scattered from the target is compared against the generated light. The difference in optical frequency between the sample and local oscillator is proportional to the distance range between the laser source and the target subject.

Accuracy and precision of the FMCW method are based on generating a frequency sweep that is highly linear, where the linewidth of the laser source, at any point along the range of swept frequencies, is extremely narrow. Compared against swept-source OCT, with linewidths ranging from around 0.01-0.03 nm, the typical linewidth of the laser source for FMCW imaging is about 0.00001 nm. The coherence length of the laser source is inversely proportional to the linewidth. Thus, the narrower the linewidth, the longer the laser coherence length and, correspondingly, the longer the ranging distance. According to an exemplary embodiment, each generated frequency in the range can have a linewidth of less than IMHz. Preferably, a ranging distance less than 2 cm for intraoral, and preferably a ranging distance greater than 0.5 m for extraoral or external imaging.

The resolution of the FMCW measurement is coarser than that provided using OCT. OCT has typical resolution in the range of about 2-15 microns. By contrast, FMCW resolution values are about 150 microns, with improved resolution down to about 10 microns achievable using peak detection techniques.

While SS-OCT (swept-source OCT) has bandwidths for swept wavelengths in the range from about 10-100 nm, FMCW has a narrower bandwidth for the swept frequency signal, typically ranging about 2-5 nm.

With coarser resolution and lacking the capability for providing depth information, FMCW has been considered inferior to OCT for dental imaging applications that are directed to diagnostic function and highly localized assessment of tissue to some depth below the surface. However, Applicants have found that FMCW capabilities can be useful for specific purposes, such as for obtaining dental impression data directly using digital imaging. Unlike OCT devices, FMCW probe hardware can be streamlined and simplified, allowing a smaller overall dimensional footprint. Thus, according to certain exemplary method and/or apparatus embodiments of the present disclosure, there is provided dental imaging (e.g., intraoral and/or extraoral) for surface imaging using Frequency-Modulated Continuous-Wave (FMCW) interferometry.

The schematic diagram of FIG. 1 shows components of a dental 3-D imaging apparatus 100 using FMCW interferometry. A FMCW image acquisition apparatus 50, alternately termed an imager or imaging engine, is in optical communication with an interferometer apparatus 10 over an optical wave guide 40, such as an optical fiber. Sample S can include one or more teeth and surrounding features.

FMCW image acquisition apparatus 50 is also in signal communication with interferometer apparatus 10 for providing power and control signals. Interferometer apparatus 10 is, in turn, in signal communication with a processor 70, such as a computer or dedicated host processor, provided with a display 72 for display of acquired and processed image content.

Figure 2A:
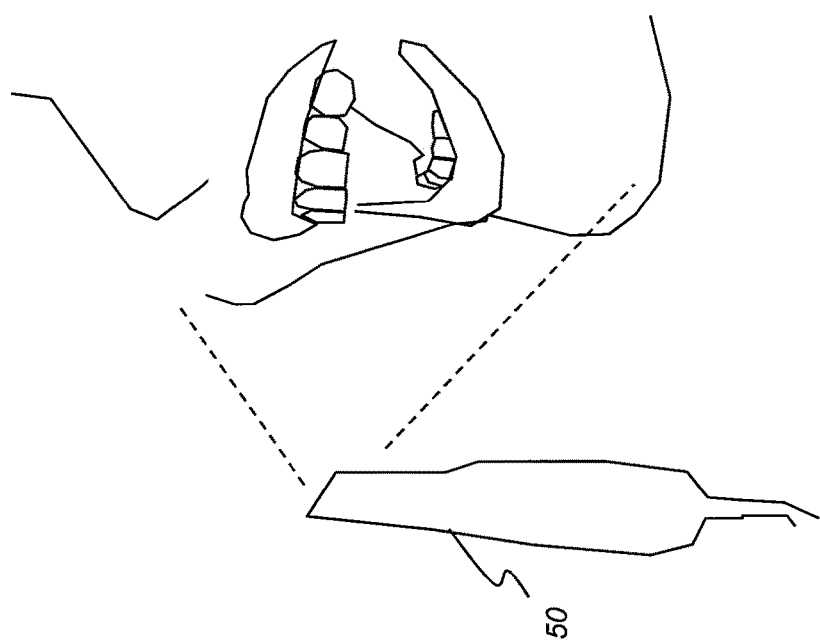
FIGS. 2A and 2B show how an FMCW image acquisition apparatus can be used for obtaining surface data from different distances for supporting digital impression and related applications.
Figure 2B:
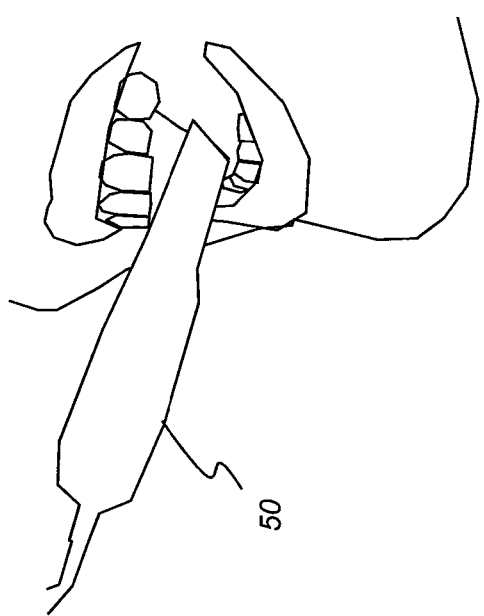

FIGS. 2A and 2B show how FMCW image acquisition apparatus 50 can be used for obtaining surface data from different distances for supporting digital impression and related applications. FIG. 2A shows the use of FMCW image acquisition apparatus 50 of dental imaging apparatus 100 for acquiring extraoral surface image data from a position outside the mouth of the patient. FIG. 2B shows the alternative use of the FMCW image acquisition apparatus 50 of the same dental imaging apparatus 100 for close-up imaging within the mouth of the patient. For this alternative use, the focal distance of FMCW image acquisition apparatus 50 is accordingly decreased by a variable-focus lens, for example a voltage-controlled variable-focus lens such as one or more liquid lens; the scanning angle of image acquisition apparatus 50 may also be accordingly changed. As FIGS. 2A and 2B show, the imaging distance of the FMCW image acquisition apparatus 50 is widely variable, allowing the same device to provide information for surface characterization of overall tooth, jaw, and facial structure as well as for characterization of particular surfaces for intraoral and extraoral features. By simple adjustment of focal distance and scanning angle, it is possible to generate surface image content for a single tooth as well as for a sizable portion of the face or jaw, e.g., using the same dental imaging apparatus 100.

Figure 3:
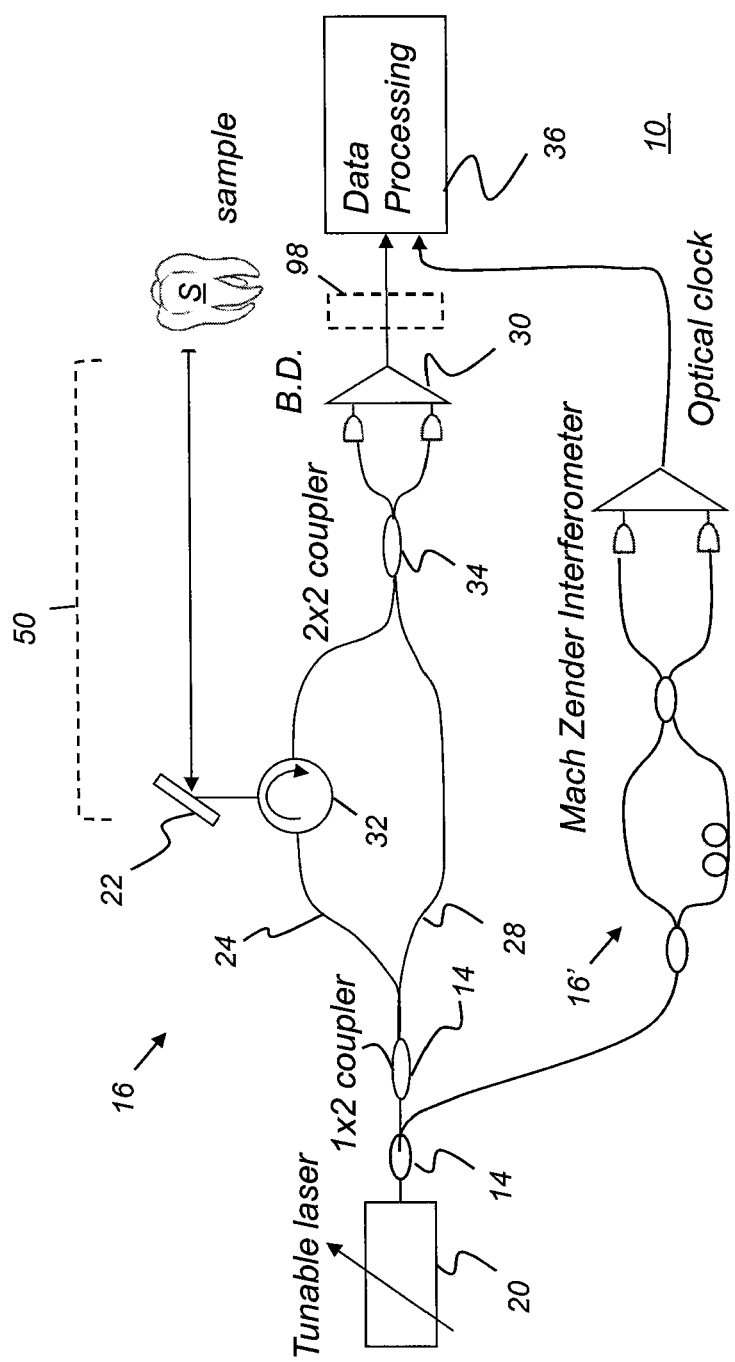
FIG. 3 is a schematic diagram that shows components of an apparatus for FMCW measurement.

The schematic diagram of FIG. 3 shows components of interferometer apparatus 10 for acquiring FMCW data from a sample S. A tunable laser diode 20 provides a variable frequency monochromatic output light signal to coupler 14 components that provide a small portion of the light to an interferometer 16', which has fixed path length difference to provide an optical clock for the data acquisition, so that the acquired signal is linear in frequency. A second 1×2 coupler 14 splits the remaining light along two paths of another interferometer 16: a sample path 24 and a reference local oscillator path 28. The light along the reference path 28 is directed to a 2×2 coupler 34 that provides the local oscillator signal to a detector 30 such as a balanced detector (B.D.) or the like. Light along sample path 24 goes to a circulator 32 and from a scanner 22 to sample S. Returned light reflected from sample S goes back to circulator 32 and to 2×2 coupler 34, then on to the detector 30. A processor 36 obtains a range measurement according to the interference signals from sample and local oscillator reference paths 24 and 28 that are combined at coupler 34 and detected by detector 30.

Tunable laser source 20 is energizable to generate a light signal that is modulated in frequency. An exemplary tunable laser source is an external cavity diode laser from Thorlabs, Newton, N.J. or a tunable pulse fiber from idealphotonics, Vancouver, Canada. The laser source can be based on Littrow or Littman model configurations. Other examples of tunable laser sources include distributed feedback lasers and tunable vertical cavity surface-emitting lasers. For selected exemplary embodiments, a variable-focus lens as described herein, can be located between the circulator 32 and the scanner 22 or located between the scanner 22 and a sample S as shown in FIG. 3.

According to an exemplary embodiment, the modulated light frequency from tunable laser source 20 is swept in a linear progression and follows a sawtooth profile with respect to time. As the signal propagates through sample S, scattering and reflection direct a portion of the signal back to detector 30 that detects interference between the returned signal from the sample and local oscillator signals, as described in more detail subsequently. Alternately, the modulated frequency can have a triangular profile, or other suitable cyclical characteristic profile, with respect to time.

As shown in FIG. 3, an optional demodulation and low pass filter 98 can be provided at the output signal from the detector 30 for selectively acquiring only a portion of the detected data, as described in more detail subsequently. In one exemplary embodiment, a detector can include detector 30 and optional demodulation and low pass filter 98. In another exemplary embodiment, a detector can include detector 30, but a capability of the optional demodulation and low pass filter 98 can be separate therefore.

Interferometer Types

Figure 4A:
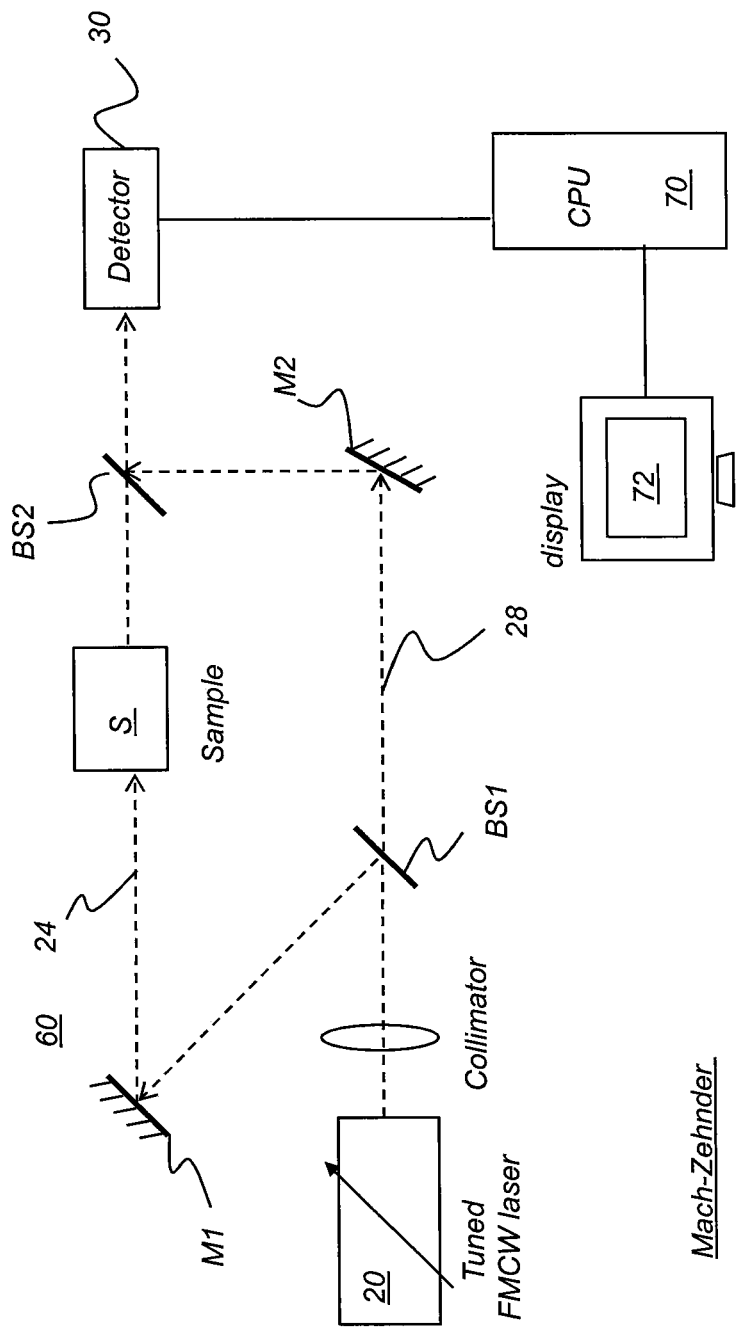
FIG. 4A is a schematic showing the interferometer of the image acquisition apparatus with a Mach-Zehnder configuration.

The simplified schematic diagram of FIG. 4A shows an optical arrangement for a Mach-Zehnder interferometer 60 for FMCW imaging of a sample S. Light from tunable laser source 20 is split into a local oscillator path 28 and a sample path 24. A beam splitter BS1 is shown for directing light into the two paths 28 and 24. Mirrors M1 and M2 fold the optical path as needed for compactness in both sample and local oscillator paths 24, 28. Light from sample S and from local oscillator path 28 is combined by a second beam splitter BS2 in order to form an interference pattern that is sensed by detector 30, such as a balanced detection photodiode.

Figure 4B:
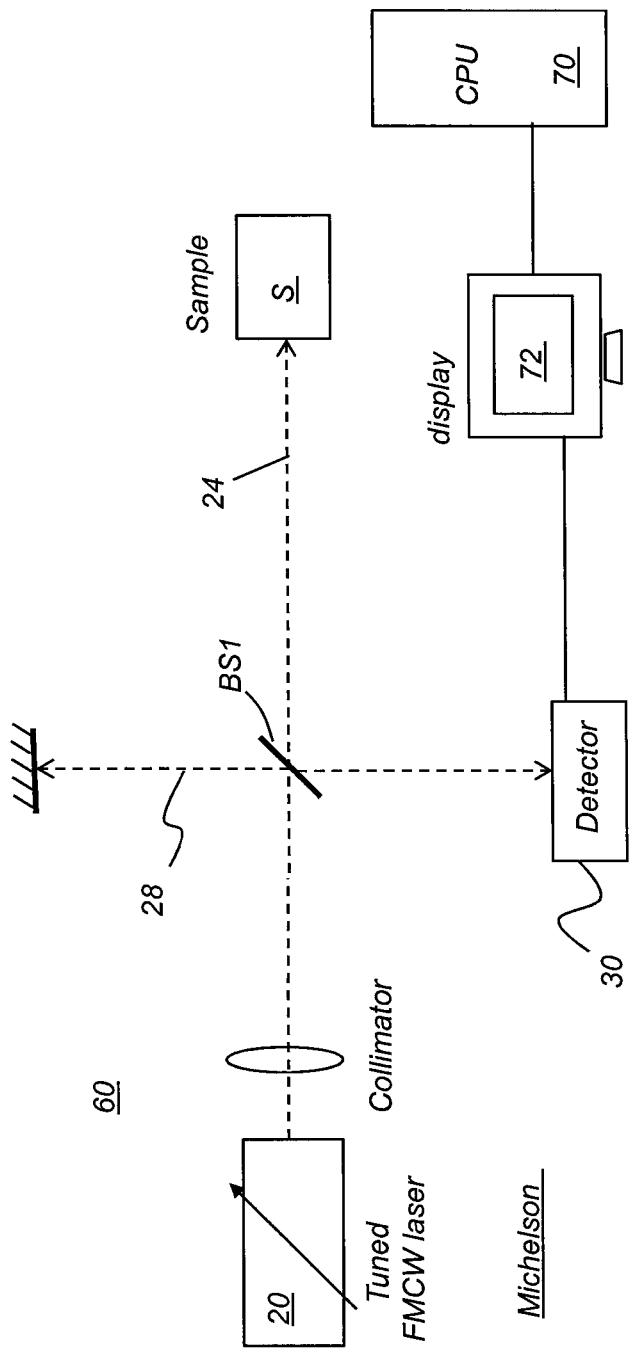
FIG. 4B is a schematic showing the interferometer with a Michelson configuration.

Certain exemplary method and/or apparatus embodiments for intraoral imaging apparatus 100 using FMCW interferometry 16 can use any suitable interferometry model such as the Mach-Zehnder interferometer model shown in FIG. 4A or the Michelson interferometer 60 as shown in FIG. 4B. In the FIG. 4B embodiment, the sample path uses beam splitter BS1 to route the local oscillator and sample signal to and from sample S. In the Michelson arrangement of FIG. 4B, the signal goes directly to sample path 24 and local oscillator path 28; the sampled signal is directed back through beam splitter BS1 to detector 30.

Signal Characteristics and Timing

Figure 5:
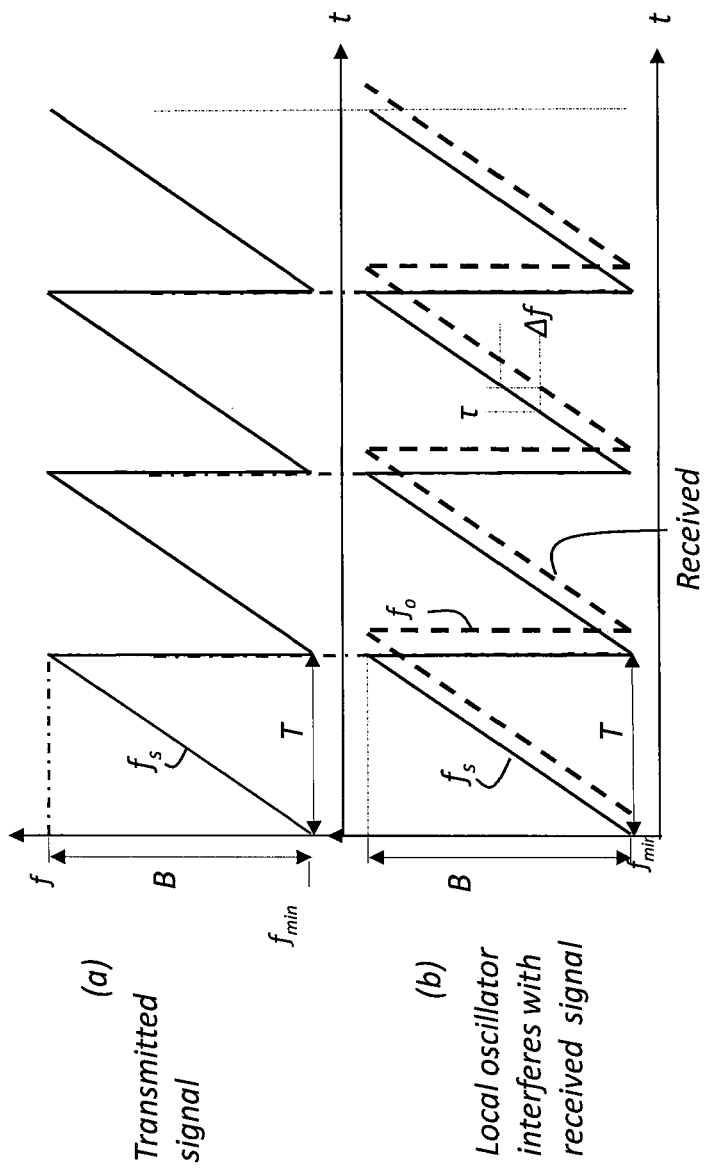
FIG. 5 is a timing diagram that shows signal content for frequencies combined using the optical path shown in FIGS. 3-4B.
Figure 6:
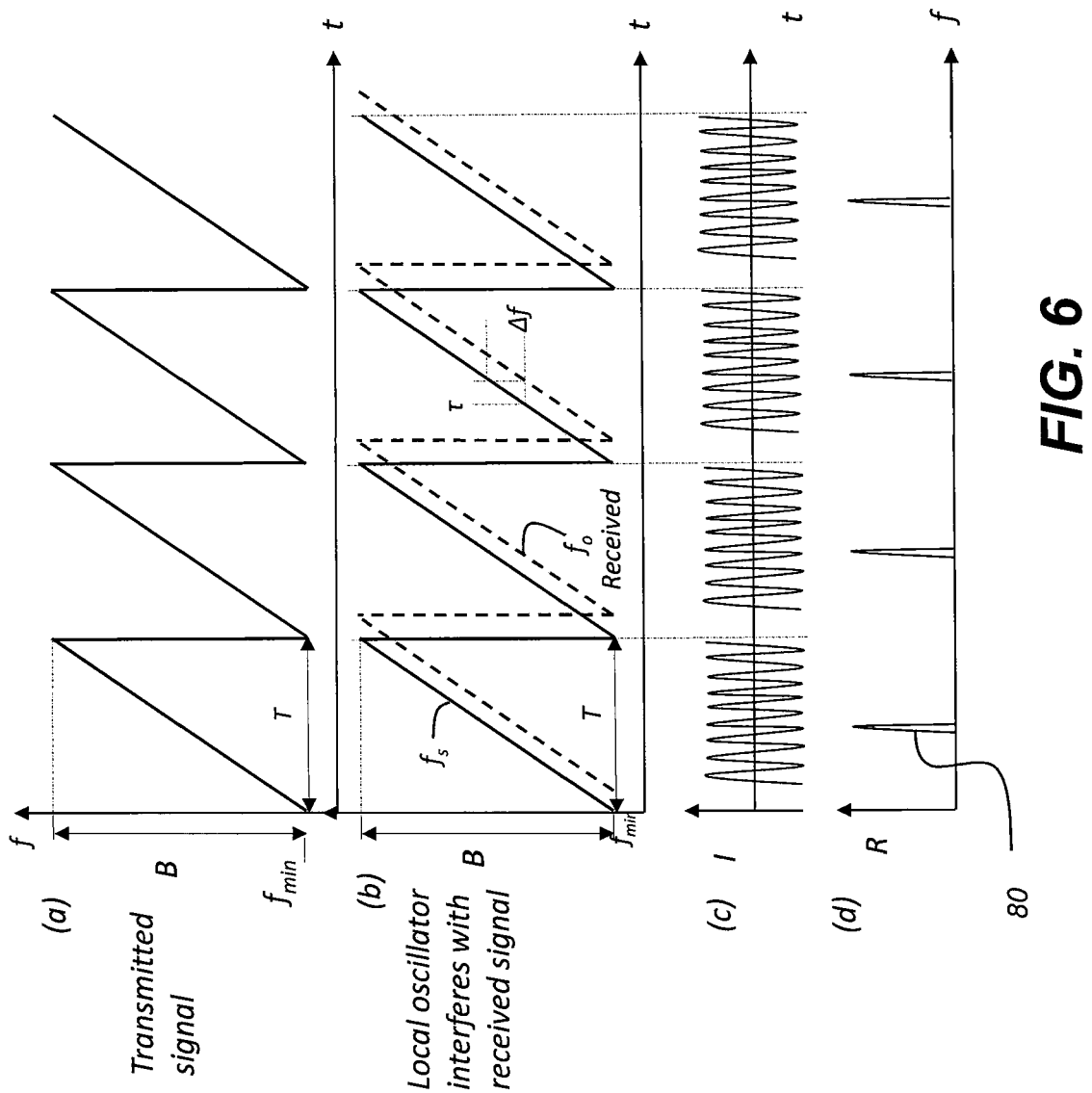
FIG. 6 is a timing diagram that shows processing of the combined frequency content to obtain distance data using the beat frequencies generated using the timing of FIG. 5.

The schematic diagram of FIG. 5 shows a characteristic frequency sweep of the light signal relative to time t that can be generated and acquired for FMCW interferometry. FIG. 6 then combines this signal information with more detailed information on signal filtering, demodulation and detection processing.

Referring to FIG. 5 part (a), the transmitted signal for FMCW imaging is a swept frequency light signal that serves as the local oscillator signal. For the FIG. 5 example, light with a sawtooth frequency sweep of period T is generated by the tunable laser diode 20 in part (a); other frequency sweep patterns could alternately be used, such as a triangular or sinusoidal pattern, for example. The sawtooth frequency sweep has sweep period T, during which frequency increases and measurements can be acquired from the combined local oscillator and sampled signals, and a restore period, where frequency drops back to a starting frequency $f_{min}$ for the next sweep interval. Frequency is plotted along the vertical y axis; time is plotted along the horizontal x axis. Value B indicates the bandwidth of the sweep. In each frequency sweep cycle T, the light frequency is varied over the bandwidth range B from a first (e.g., minimum frequency value $f_{min}$) to a second (e.g., maximum frequency value f).

For a sweep over a selected or the full modulation bandwidth B from frequency $f_{min}$, the emitted signal from the source is:

$$s(t) = E_s \exp(i2\pi ft) = E_s \exp(i2\pi(f_{min} + Bt/T)t) \quad (1)$$

wherein $E_s(f)$ is the spectrum profile weight of a function optical frequency f; $f_{min}$ is the minimum optical frequency; Bt/T is the linear sweep of frequency with bandwidth B.

In FIG. 5 part (b) the timing difference or delay between frequencies of the local oscillator signal $f_s$ and the received signal $f_o$ from the sample is shown as value τ, a measure of the phase difference between sample and local oscillator signals as these signals interfere and are directed to detector 30 of FIG. 3. Value Δf shows the frequency difference between the local oscillator signal $f_s$ and the received signal $f_o$ from the sample at a particular time.

In the object or sample path, the light is incident on the sample and backscattered. The received reflectance R(t) is a copy of emitted signal with round trip time delay τ=2R/C, where R is the distance range to the target and C is the speed of light:

$$R(t,\tau) = E_r \exp(i2\pi(f_{min} + B(t-\tau)/T)(t-\tau)). \quad (2)$$

R(f) is the reflected spectral profile. This signal interferes with the local oscillator reference signal. The interference from their combination produces the following beat signal I(t, τ):

$$I(t, \tau) = (R(t, \tau) + S(t))(R(t, \tau) + S(t))^* = \quad (3)$$

$$E_s^2 + E_r^2 + 2E_sE_r\cos(2\pi f_{min}\tau + 4\pi Bt\tau/T - 2\pi B\tau^2/T) =$$

$$E_s^2 + E_r^2 + 2E_sE_r\cos(\varphi + 4\pi f_m t\tau)$$

wherein $f_m$ is the frequency modulation rate equal to B/T. A Fourier transform on the obtained signal generates the beat frequency signal E(τ):

$$E(\tau) \propto \int I(t,\tau) e^{-i2\pi f_m \alpha t} dt \quad (4)$$

This signal represents reflected light at time delay τ.

FIG. 6 part (c) shows the beat signal I from detector 30. Data for a single point on the surface of the sample S is acquired during each sweep period T. FIG. 6 part (d) shows a processed beat signal 80 that is generated from the beat signal I, for example, at detector 30. Fourier transform processing can generates the processed beat signal 80 which gives a distance value R that provides spatial location information for the scanned point on the sample surface. With the timing shown, each sweep cycle of period T has a corresponding signal acquisition time.

At FIG. 6 part (d) the processed beat signal is shown without DC terms. Thus, for each period T, a Fourier transform obtains the range signal, distance R, from the acquired beat signal I.

When the scanned subject is stationary, the beat frequency $f_b$ is:

$$f_b = 2f_m\tau = 2B\tau/T \quad (5)$$

Substituting τ=2R/C, the distance range R can extend to:

$$R = f_b \frac{T}{4B} c \quad (6)$$

According to these relationships, a Fourier transform on obtained beat signal of one sweep cycle generates the range of the object for each measured point on the sample surface.

The range resolution δ=c/2B is inversely proportional to sweep bandwidth B. The higher the bandwidth B, the finer the spatial resolution. For a dental digital impression, a selected or the required resolution is <50 μm. The corresponding bandwidth for this resolution value is >3000 GHz (B=c/2 δ).

According to an exemplary embodiment of the present disclosure, a MEMS scanner performs the raster scanning, directing the signal shown in FIG. 6 at (a) as a collimated narrow-linewidth beam to the teeth. Each scan point correspondingly receives the full sweep of optical frequencies of bandwidth B. The beat signal between the local oscillator reference and reflected signal from the surface of sample S is acquired by the detector 30 (FIG. 3).

As shown in FIG. 3, optional demodulation and low pass filter 98 can be provided the signal from the detector 30. The demodulation and low pass filter 98 can analyze or move the signal to low frequency. The low-frequency bandpass filter can selectively filter out frequencies from the beat signal that have little or no effect on the processed range data. Thus, for example, only a portion of the beat signal would require processing, simplifying the computation of range data.

Figure 7:
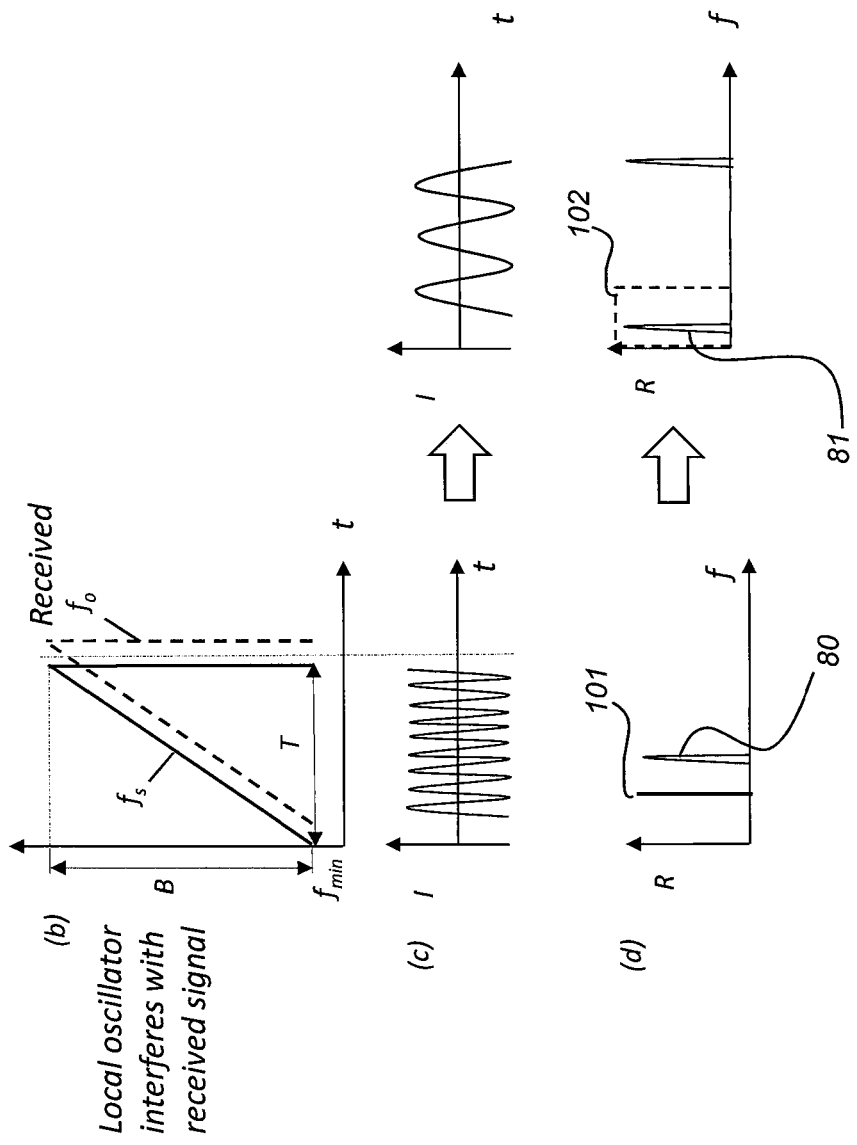
FIG. 7 shows use of an optional demodulation and low pass filter to isolate particular frequencies for beat frequency analysis.

When using a filter of this type, the beat signal I of FIG. 7 part (c) mixes with another resonant signal, providing demodulation by moving the beat signal of FIG. 7(c) to a lower frequency band, as shown. This is effected by multiplying by $\cos(2\pi f_d t)$. The demodulated signal then goes through a lowpass filter which selects the desirable distance range. The following sequence shows the processing procedure.

$$I(t, \tau) = E_s^2 + E_r^2 + 2E_sE_r\cos(\varphi + 4\pi f_m t\tau) \xrightarrow{balance\ detection} \quad (7)$$

$$2E_sE_r\cos(\varphi + 4\pi f_m t\tau) \xrightarrow{demodulation\ by\ 2\cos(2\pi f_d t)}$$

$$4E_sE_r\cos(\varphi + 4\pi f_m t\tau)\cos(2\pi f_d t) =$$

$$2E_sE_r\cos(\varphi + 2\pi(2f_m\tau - f_d)t) +$$

$$2E_sE_r\cos(\varphi + 2\pi(2f_m\tau + f_d)t) \xrightarrow{low\ pass\ filter}$$

$$2E_sE_r\cos(\varphi + 2\pi(2f_m\tau - f_d)t)$$

Then, using a standard reconstruction computation FFT, the beat frequency becomes $$f_b = 2f_m\tau - f_d = 2B\tau/T - f_d \quad (8)$$

Substituting $\tau = 2R/C$, the distance range R can extend to:

$$R = (f_b + f_d)\frac{T}{4B}c \quad (9)$$

The graph of FIG. 7 shows the effect of demodulation and low pass filter 98 for defining a region of interest relative to transmitted and received frequency signals, as shown at 101 and at dashed box 102. Mixing signal has frequency $f_d$ shown as frequency 101. After mixing, a low pass filter with pass band, as shown in a box 102, is applied. Signals outside the filter transmission range are suppressed. The selected frequencies passing through filter 98 are then used for Fourier transform processing that can generate processed beat signal 80. This can reduce the amount of data that must be processed, such as by a fast Fourier transform (FFT).

Demodulation with frequency $f_d$ is first applied to the acquired beat signal I of FIG. 7 part (c). The frequency domain representation is shown as 101 in FIG. 7 part (d). Frequency adjustment can be used to move reconstructed beat signal 81 to low frequency band and higher frequency band, providing the peaks shown in FIG. 7(*d*), with one peak situated at low frequency, with the other peak at a high frequency band. A low pass filter is applied to select the lower frequency band, providing the lower frequency signal shown in the progression of FIG. 7(*c*). The lower frequency signal is acquired, saved, and processed. Note that this signal conditioning, over a shorter length and using relatively slow speed signal digitization, is allowable based on the Nyquist-Shannon sampling theorem.

The reconstructed beat signal 81 is shown in a dashed box 102 in FIG. 7(*d*). Then a constant shift with $f_d$ is applied in order to shift signal 81 back to correct position shown with the processed beat signal 80. Peak detection can be applied to the reconstructed signal or the processed beat signal 80 to result in greater accuracy in object ranging.

Scanning the Sample

Figure 8:
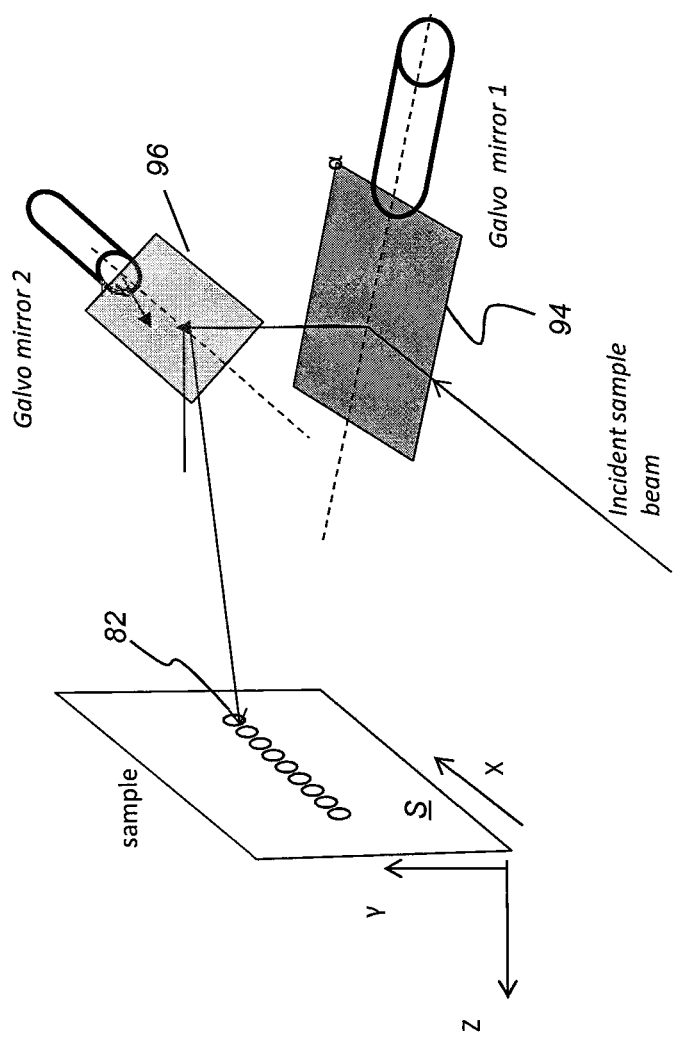
FIG. 8 shows scanning action using two galvo mirrors.

Referring to FIG. 8, scanner 22 can be a micro-electro-mechanical system (MEMS) device that provides one or more mirrors or other light redirection optics for directing light to sample S using a raster scan pattern.

As shown in the schematic diagram of FIG. 8, galvo mirrors 94 and 96 cooperate to provide the raster scanning needed for FMCW imaging. In the arrangement that is shown, galvo mirror 1 (94) scans the modulated light, in the x direction as shown, to each point 82 along the sample S to generate data along a row. Galvo mirror 2 (96) progressively moves the row position in they direction to provide 2-D raster scanning to additional rows. At each point 82, the full cycle of light frequencies shown in FIGS. 5 and 6 are generated to provide spatial position information related to that point.

Figure 9:
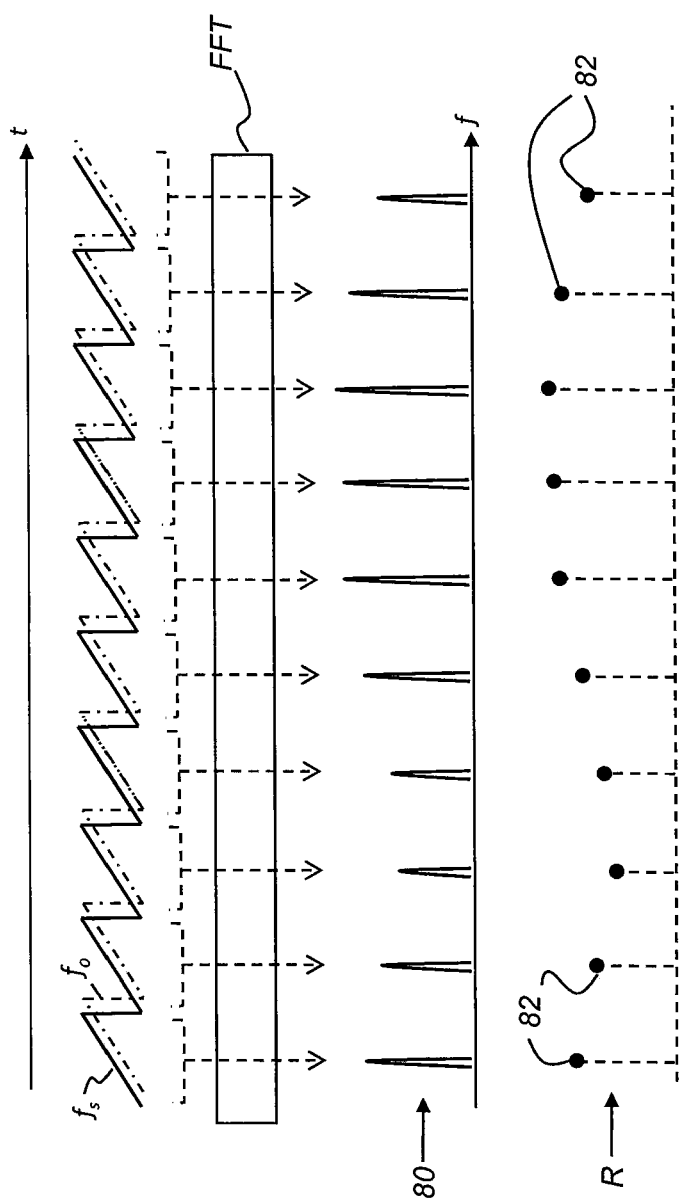
FIG. 9 is a schematic diagram that shows a sequence for generating a line of points using the method and apparatus of the present disclosure.

The schematic diagram of FIG. 9 shows how the image processing software of processor 70 (FIG. 1) can operate on the scanned FMCW frequency data in order to obtain a line of points 82 for generating a point cloud that characterizes a portion of the surface contour of the sample S. Interference with received signal $f_o$ at each ramped sweep of laser frequencies $f_s$ generates beat frequency content that is processed by fast Fourier transform FFT to obtain the corresponding processed beat signal 80 that provides corresponding range data for calculating distance R for successive points along a scanned line of the sample. Each point 82 in the point cloud has a value of R computed using this technique, preferably obtained from the peak value of the processed beat signal 80. As represented schematically in FIG. 10, scanning of successive lines then generates a point cloud C characterizing the 3D surface of sample S.

Consistent with exemplary embodiments herein, a computer program can use stored instructions that perform on image data that is accessed from an electronic memory. As can be appreciated by those skilled in the image processing arts, a computer program for operating the imaging system and probe and acquiring image data in exemplary embodiments of the application can be utilized by a suitable, general-purpose computer system operating as CPU 70 as described herein, such as a personal computer or workstation. However, many other types of computer systems can be used to execute the computer program of the present invention, including an arrangement of networked processors, for example. The computer program for performing exemplary method embodiments may be stored in a computer readable storage medium. This medium may include, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary method embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products of the application may make use of various image manipulation algorithms and processes that are well known. It will be further understood that computer program product exemplary embodiments of the application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product exemplary embodiments of the application, are not specifically shown or described herein and may be selected from such algorithms, systems, hardware, components and elements known in the art.

Certain exemplary method and/or apparatus embodiments of the application can provide surface contour images by employing Frequency-Modulated Continuous-Wave interferometry in a hand-held imaging camera (e.g., intraoral) to characterize surfaces of teeth, gum tissue, and other intraoral features and/or in the hand-held imaging camera to characterize surfaces of a face or features thereof (e.g., extraoral or facial scanning). Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. An apparatus for oral imaging comprising:
   a) a tunable laser source energizable to generate a light frequency signal that ranges from a first frequency to a second higher frequency, wherein each generated frequency in the range has a linewidth of less than 1 MHz;
   b) an image acquisition apparatus that is energizable to scan the generated light frequency signal to each of a plurality of successive positions on a and to combine a returned signal from said each of the plurality of successive positions on the sample surface with the generated light frequency signal, the image acquisition apparatus comprising a detector that obtains a beat frequency signal corresponding to each scanned successive position from a combination of the returned signal and the generated light frequency signal;
   c) a processor that is in signal communication with the detector and that generates a processed beat signal from the obtained beat frequency signal, where the processed beat signal is indicative of a distance from the image acquisition apparatus to the sample surface at the corresponding scanned position; and
   d) a display that is in signal communication with the processor and is energizable to display distance data according to the processed beat signal for each scanned position.

2. The apparatus of claim 1 wherein the tunable laser source is an external cavity diode laser.

3. The apparatus of claim 1 wherein the detector is a balanced detector.

4. The apparatus of claim 1 wherein the range has a bandwidth of about 2-5 nm.

5. The apparatus of claim 1 wherein the tunable laser source bandwidth exceeds 3000 GHz.

6. The apparatus of claim 1 further comprising a low-pass filter at the output of the detector for selecting frequencies used to generate the processed beat signal.

7. The apparatus of claim 1 wherein the distance data displays as a point cloud.

8. The apparatus of claim 1 wherein the image acquisition apparatus is a handheld device.

9. The apparatus of claim 1 wherein the range of light frequencies are swept in a linear time progression.

10. A method for oral imaging comprising:
    a) energizing a tunable laser source to generate a light frequency signal over a range of light frequencies from a first frequency to a second different frequency, wherein each generated frequency in the range has a linewidth of less than 1 MHz;
    b) energizing an image acquisition apparatus to scan the generated light frequency signal to successive positions on a sample surface in the mouth of a patient and to combine a return signal corresponding to each successive position with the generated light frequency signal;
    c) obtaining a beat frequency signal from the combined returned signal and generated light frequency signal;
    d) processing the obtained beat frequency signal to generate a processed beat signal that is indicative of a distance from the tunable laser source to the sample surface at the corresponding position; and
    e) generating a display that represents the distance for each scanned position on the oral sample surface.

11. The method of claim 10 wherein generating the display comprises displaying a point cloud or a 3D polygonal mesh of an intraoral feature of dentition.

12. The method of claim 10 further comprising energizing the image acquisition apparatus to scan the generated light frequency signal to successive surface positions outside the mouth of a patient and to combine an extraoral return signal corresponding to each successive position with the generated light frequency signal for obtaining a beat frequency signal.

13. The method of claim 12 further comprising characterizing a surface of a jaw, a facial feature, or a face of a patient according to the combined extraoral return signal and the generated light frequency signal.

14. The method of claim 10 wherein the successive positions are scanned from a single location and further include positions outside the mouth of the patient.

15. The method of claim 13 further comprising the use of a variable-focus lens.

16. The method of claim 10 wherein the range has a bandwidth of about 2-5 nm.

17. The method of claim 10 wherein the tunable laser source bandwidth exceeds 3000 GHz.

* * * * *